United States Patent
Jaffe et al.

(10) Patent No.: US 10,094,810 B2
(45) Date of Patent: Oct. 9, 2018

(54) SYSTEM AND METHOD FOR MONITORING COMPOSITION IN A SIDESTREAM SYSTEM USING A DISPOSABLE SAMPLING CHAMBER

(71) Applicant: KONINKLIJKE PHILIPS N.V., Eindhoven (NL)

(72) Inventors: Michael Brian Jaffe, Cheshire, CT (US); David Scampoli, South Glastonbury, CT (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/356,412

(22) PCT Filed: Nov. 2, 2012

(86) PCT No.: PCT/IB2012/056111
§ 371 (c)(1),
(2) Date: May 6, 2014

(87) PCT Pub. No.: WO2013/068899
PCT Pub. Date: May 16, 2013

(65) Prior Publication Data
US 2014/0326048 A1   Nov. 6, 2014

Related U.S. Application Data

(60) Provisional application No. 61/556,370, filed on Nov. 7, 2011.

(51) Int. Cl.
G01N 33/00   (2006.01)
A61B 5/08   (2006.01)
(Continued)

(52) U.S. Cl.
CPC ......... *G01N 33/0027* (2013.01); *A61B 5/082* (2013.01); *A61B 5/083* (2013.01);
(Continued)

(58) Field of Classification Search
CPC .......................... A61B 5/082; G01N 33/0027
See application file for complete search history.

(56) References Cited

U.S. PATENT DOCUMENTS

| 4,370,553 A | 1/1983 | Waycaster et al. |
| 4,519,792 A * | 5/1985 | Dawe ........................... 604/152 |

(Continued)

FOREIGN PATENT DOCUMENTS

| WO | 2010128914 A1 | 11/2010 |
| WO | 2012146991 A1 | 11/2012 |

*Primary Examiner* — Lisa Caputo
*Assistant Examiner* — Alex Devito

(57) ABSTRACT

A detector to measure composition of a flow of gas from a respiratory circuit. The detector includes a housing and a removable flow path element. The removable flow path element includes an inlet, a sampling chamber, a pump section including a membrane and an actuator interface, and an outlet. A flow path element dock is formed by the housing with the flow path element dock to removably engage the removable flow path element. A radiation source within the housing emits radiation into a sampling chamber of the removable flow path element while the removable flow path element is docked in the flow path element dock. A sensor is housed within the housing. A pump actuator and controller are within the housing to drive the pump to maintain the flow rate of the flow of breathable gas through an enclosed flow path.

22 Claims, 13 Drawing Sheets

(51) Int. Cl.
  *A61B 5/083* (2006.01)
  *A61B 5/097* (2006.01)
  *G01N 21/61* (2006.01)
  *G01N 21/85* (2006.01)

(52) U.S. Cl.
  CPC ............ *A61B 5/097* (2013.01); *G01N 21/61* (2013.01); *G01N 21/85* (2013.01); *A61B 5/0836* (2013.01); *A61B 2560/0456* (2013.01); *G01N 2021/8578* (2013.01)

(56) References Cited

U.S. PATENT DOCUMENTS

| | | | |
|---|---|---|---|
| 4,692,621 A | | 9/1987 | Passaro et al. |
| 4,794,922 A | * | 1/1989 | DeVries ................ A61M 16/00 128/204.18 |
| 4,958,075 A | | 9/1990 | Mace et al. |
| 5,060,656 A | * | 10/1991 | Howard ................ G01N 33/497 600/531 |
| 5,103,212 A | | 4/1992 | Notarianni et al. |
| 6,325,978 B1 | | 12/2001 | Labuda et al. |
| 6,632,402 B2 | | 10/2003 | Blazewicz et al. |
| 7,040,183 B2 | | 5/2006 | Castor et al. |
| 7,294,839 B2 | | 11/2007 | Rich et al. |
| 7,341,563 B2 | | 3/2008 | Rich et al. |
| 7,556,039 B1 | | 7/2009 | Pierry |
| 7,748,280 B2 | | 7/2010 | Jaffe et al. |
| 2002/0036266 A1 | * | 3/2002 | Dreyer ................ G01N 21/3504 250/345 |
| 2003/0138329 A1 | | 7/2003 | Koyano et al. |
| 2003/0191405 A1 | * | 10/2003 | Rich ...................... A61B 5/097 600/532 |
| 2004/0000643 A1 | * | 1/2004 | Karlsson ................ G01N 21/61 250/339.13 |
| 2007/0235405 A1 | * | 10/2007 | Al-Thallab ................ 215/11.1 |
| 2008/0041172 A1 | | 2/2008 | Jaffe et al. |
| 2009/0062673 A1 | | 3/2009 | Scampoli |
| 2010/0065053 A1 | * | 3/2010 | Haveri ............... A61M 16/0833 128/204.18 |
| 2012/0051956 A1 | * | 3/2012 | Grip .................... A61M 5/1413 417/413.1 |
| 2014/0326048 A1 | | 11/2014 | Jaffe et al. |

* cited by examiner

SYSTEM AND METHOD FOR MONITORING COMPOSITION IN A SIDESTREAM SYSTEM USING A DISPOSABLE SAMPLING CHAMBER

CROSS-REFERENCE TO PRIOR APPLICATIONS

This application is the U.S. National Phase application under 35 U.S.C. § 371 of International Application No. PCT/IB2012/056111, filed on Nov. 2, 2012, which claims the benefit of U.S. Provisional Patent Application No. 61/556,370, filed on Nov. 7, 2011. These applications are hereby incorporated by reference herein.

BACKGROUND

1. Field

The present disclosure pertains to a method and apparatus for monitoring the composition of a measurement flow of breathable gas received in a sidestream manner from a flow of breathable gas being delivered to the airway of a subject through a respiratory circuit.

2. Description of the Related Art

Systems that monitor composition of gas by obtaining a measurement flow of breathable gas from a therapeutic flow of breathable gas in a sidestream manner are known. Generally, these systems require a pump to draw the measurement flow of breathable gas through a sampling chamber where measurements are taken. The measurement flow of breathable gas is then exhausted from the system (e.g., to atmosphere and/or through a filter or captured by a scavenging system). Generally, the measurement flow of breathable gas is not returned to the therapeutic flow of breathable gas because this would require that the elements of the pump exposed to the measurement flow of breathable gas be either disposed of or thoroughly sterilized for individual subjects. This may be impractical and/or cost prohibitive.

SUMMARY

Accordingly, one or more aspects of the present disclosure relate to a detector device configured to measure composition of a flow of breathable gas received from a respiratory circuit. In some embodiments, the detector device comprises one or more of a housing, a flow path element dock, a radiation source, a sensor assembly, a pump actuator, and/or a controller. The flow path element dock is formed by the housing, and is configured to removably engage a flow path element having an inlet and an outlet. The flow path element forms an enclosed flow path for the flow of breathable gas. The radiation source is housed within the housing and configured to emit electromagnetic radiation into the flow path element while the flow path element is docked in the flow path element dock. The sensor assembly is housed within the housing and configured such that, while the flow path element is docked in the flow path element dock and the radiation source emits electromagnetic radiation into the flow path element, the sensor assembly receives electromagnetic radiation that has been emitted by the radiation source and has passed through the flow path formed in the flow path element. The sensor assembly is further configured to generate an output signal conveying information related to one or more parameters of the received electromagnetic radiation. The pump actuator is carried by the housing configured to actuate one or more components of the flow path element to draw flow of breathable gas through the enclosed flow path. The controller is housed within the housing configured to control the pump actuator to maintain the flow rate of the flow of breathable gas through the enclosed flow path.

Yet another aspect of the present disclosure relates to a method of measuring the composition of a flow of breathable gas received from a respiratory circuit. The method comprises removably docking a flow path element with a housing of a detector device, the flow path element having an inlet and an outlet, and forming an enclosed flow path therebetween; emitting electromagnetic radiation from a radiation source into the flow path element while the flow path element is docked with the housing, wherein the radiation source is housed within the housing; receiving electromagnetic radiation that has been emitted by the radiation source and has passed through the enclosed flow path of the flow path element onto a sensor assembly housed within the housing; generating an output signal conveying information related to one or more parameters of the electromagnetic radiation received onto the sensor assembly; actuating one or more components of the flow path element with a pump actuator carried by the housing to draw flow of breathable gas through the enclosed flow path; and controlling the pump actuator with a controller housed within the housing to maintain the flow rate of the flow of breathable gas through the enclosed flow path.

Still another aspect of present disclosure relates to a detector device for measuring the composition of a flow of breathable gas received from a respiratory circuit. In some embodiments, the detector device comprises means for housing the detector device; means for removably docking a flow path element with the means for housing the detector device, the flow path element having an inlet and an outlet, and forming an enclosed flow path therebetween; means for emitting electromagnetic radiation into the flow path element while the flow path element is docked with the means for housing, wherein the means for emitting is housed within the housing; means for receiving electromagnetic radiation that has been emitted by the means for emitting and has passed through the enclosed flow path of the flow path element, wherein the means for receiving is housed within the housing; means for generating an output signal conveying information related to one or more parameters of the electromagnetic radiation received onto the means for receiving; means for actuating one or more components of the flow path element to draw flow of breathable gas through the enclosed flow path, wherein the means for actuating is carried by the means for housing; and means for controlling the means for actuating to maintain the flow rate of the flow of breathable gas through the enclosed flow path.

These and other objects, features, and characteristics of the present displosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
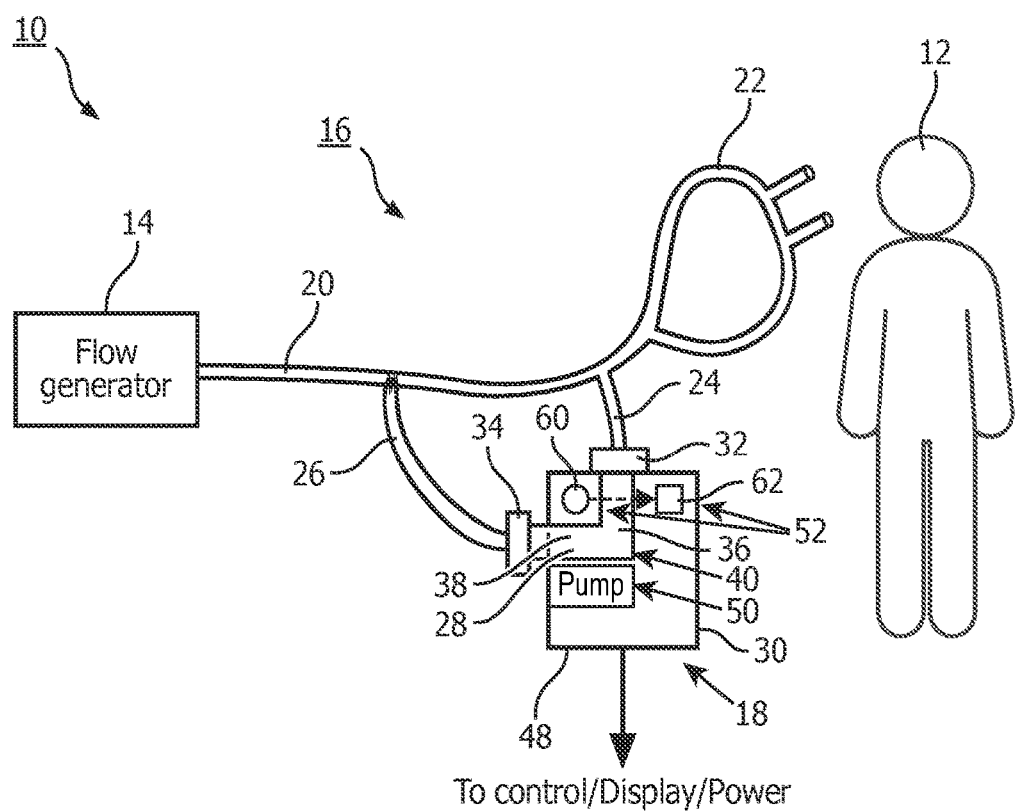
FIG. 1 is a system configured to monitor composition of a flow of breathable gas being delivered to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to monitor composition of a flow of breathable gas being provided to a subject 12. System 10 may be configured such that a measurement flow of breathable gas is diverted in order to monitor composition of the flow of breathable gas, and then the measurement flow of breathable gas is returned to the flow of breathable gas. This will tend to conserve the constituent gases within the flow of breathable gas, which may be significant in instances where the flow of breathable gas is being used to deliver medicaments or drugs (e.g., relatively expensive anesthetic, and/or other medicaments or drugs). Since the measurement flow of breathable gas will tend to have contaminants (e.g., mucus blood, medications, condensate or other materials), routing the measurement flow of breathable gas back into the flow of breathable gas constitutes a placement solution for the contaminants. In system 10, the components that contact the measurement flow of breathable gas may be disposable, in order to facilitate reintroduction of the measurement flow of breathable gas back into the flow of breathable gas. In some embodiments, system 10 may include one or more of a flow generator 14, a respiratory circuit 16, a measurement circuit 18, and/or other components.

Flow generator 14 is configured to generate the flow of breathable gas for delivery to the airway of subject 12. Flow generator 14 is configured to control one or more parameters of the flow of breathable gas. The parameter(s) controlled may include one or more of pressure, temperature, flow rate, humidity, velocity, acoustics, and/or other parameters. In some embodiments, flow generator 14 is configured to control the composition of the flow of breathable gas by blending gases from a two or more gas sources (e.g., to control oxygen content), by adding a drug or medicament (e.g., in nebulized and/or aerosolized form), and/or by other techniques. To pressurize the flow of breathable gas, flow generator 14 may include one or more of a blower, a bellows, a pressurized canister or Dewar, a wall gas source, and/or other sources of pressure.

Respiratory circuit 16 is configured to deliver the flow of breathable gas from flow generator 14 to the airway of subject 12. Respiratory circuit 16 may include one or more of a conduit 20, a subject interface 22, and/or other components. Conduit 20 is configured to convey the flow of breathable gas from flow generator 14 to subject interface 22. Conduit 20 interfaces with flow generator 14 to receive the flow of breathable gas therefrom, and provides a flow path from flow generator 14 to subject interface 22. Conduit 20 may be resiliently flexible. Subject interface 22 may engage one or more orifices of the airway of subject 12 in a sealed or unsealed manner Some examples of subject interface 22 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface. For example, sidestream gas sampling (e.g., as shown and described with respect to system 10) may be used in conjunction with an airway adapter which is in-line with both expiratory and inspiratory gases, a facemask from which a tap is often made and a nasal cannula as shown in FIG. 1 which may be used to sample a respiratory gas (e.g. CO2) and/or to deliver a therapeutic gas (e.g., oxygen).

Measurement circuit 18 is configured to draw a measurement flow of breathable gas off from the flow of breathable gas in respiratory circuit 16 to monitor the compositions of the flow of breathable gas. The measurement flow of breathable gas may be between about 30 ml/min and about 250 ml/min. In some embodiments, the measurement flow of breathable gas is about 50 ml/min. Measurement circuit 18 may return some or all of the gas in the measurement flow of breathable gas back to the flow of breathable gas within respiratory circuit 16. Measurement circuit 18 may include one or more of a circuit inlet 24, a circuit outlet 26, a flow path element 28, a detector device 30, and/or other components.

Circuit inlet 24 is configured to receive a portion of the gas in the flow of breathable gas within respiratory circuit 16 as a measurement flow of breathable gas, and to guide the measurement flow of breathable gas to flow path element 28. Circuit outlet 26 is configured to receive the measurement flow of breathable gas after it has passed through flow path element 28. Circuit outlet 26 may be configured to provide the measurement flow of breathable gas back into respiratory circuit 16. Circuit inlet 24 and circuit outlet 26 may be conduits similar in structure (or the same as) conduit 20. Circuit outlet 26 may be a connector or not even exist if the flow is to pass into the atmosphere. The interface(s) between one or both of circuit inlet 24 and conduit 20, and circuit outlet 26 and conduit 20 may be releasable.

Figure 2:
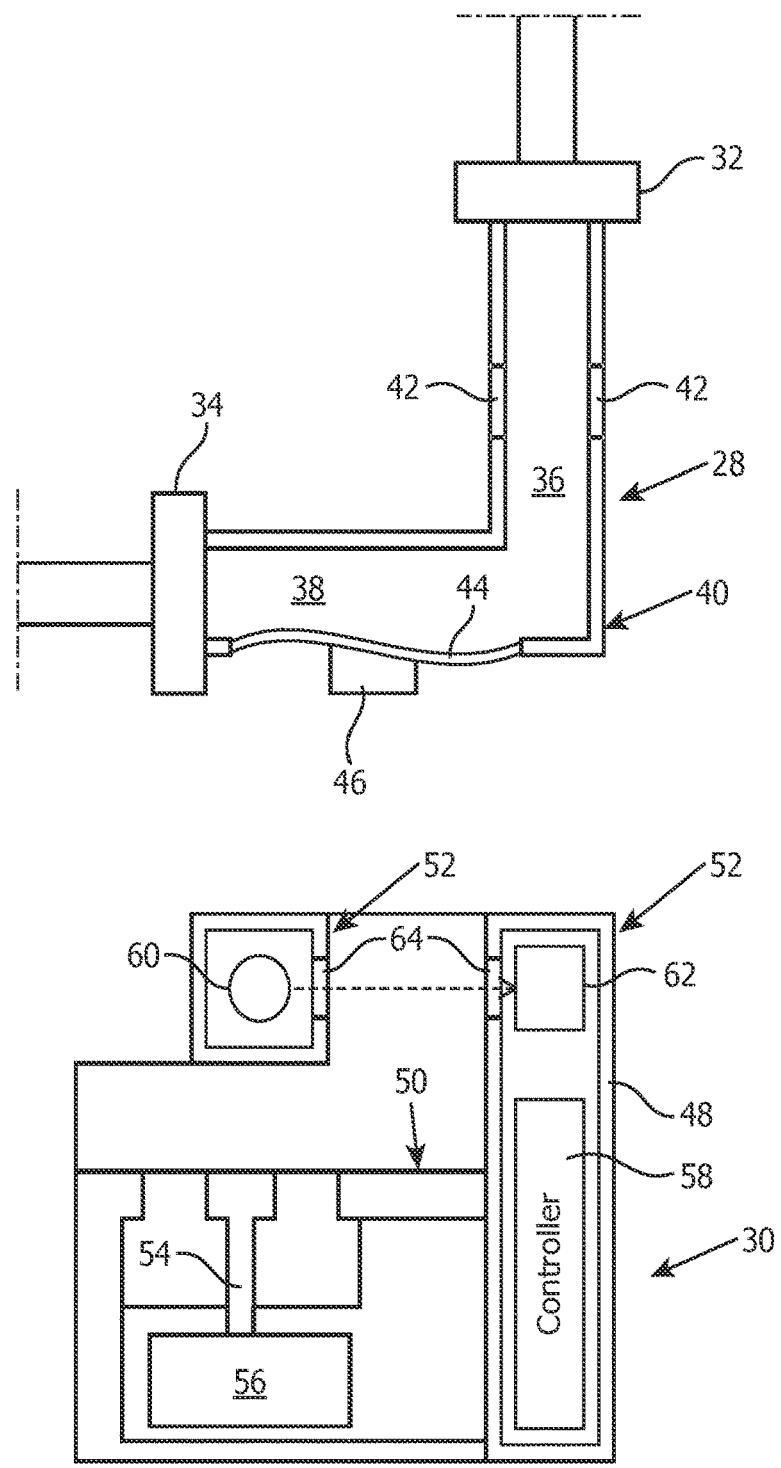
FIG. 2 is a diagram of a detector device and flow path assembly.

FIG. 2 provides a more detailed schematic of flow path element 28 and detector device 30. In the view shown in FIG. 2, flow path element 28 has been disengaged from detector device 30 (FIG. 1 depicts flow path element 28 releasably engaged with detector device 30). As can be seen in FIG. 2, flow path element 28 includes an inlet 32, an outlet 34, and provides an enclosed flow path between inlet 32 and outlet 34. Inlet 32 is configured to interface with circuit inlet 24, and outlet 34 is configured to interface with circuit outlet 26 such that the enclosed flow path formed by flow path element 28 carries the measurement flow of breathable gas through flow path element 28 from inlet 32 to outlet 34. The walls of flow path element 28 between inlet 32 and outlet 34 may be formed of substantially rigid plastic and/or polymer materials. Flow path element 28 further comprises one or more of a sampling chamber 36, a pump section 38, a device interface 40, and/or other components.

Sampling chamber 36 is configured to facilitate measurements of the composition of the measurement flow of breathable gas to be taken. As such, sampling chamber 36 includes windows 42. Windows 42 are optically transparent to electromagnetic radiation at one or more wavelengths used to measure the composition of gas within sampling chamber 36. By way of non-limiting example, windows 42 may be formed from sapphire, IR transmissive plastics, and/or other materials.

Pump section 38 is configured to generate flow through flow path element 28 from inlet 32 to outlet 34. In some embodiments, pump section 38 operates as the head of a membrane pump system to generate flow through flow path element 28. Pump section 38 may include one or more of a membrane 44, an actuator interface 46, and/or other components. Membrane 44 is configured to be movable to generate flow through pump section 38. Actuator interface 46 is configured to releasably engage a pump actuator 54 associated with detector device 30 to actuate membrane 44 in a manner that causes movement by membrane 44 resulting in flow through flow path element 28.

The enclosed flow path formed by flow path element 28 enables flow path element 28 to be used for a subject individually. This means that for another subject, and/or for another usage session, flow path element 28 can be swapped for another (e.g., new) flow path element. It will be appreciated that the components of flow path element 28 are relatively inexpensive from a materials and/or manufacturing perspective. For example, flow path element 28 does not include any sensor or radiation emitter elements, and does not include any parts of a motor that operates to drive the pump formed by pump section 38. In some embodiments, flow path element 28 does not include any processing and/or storage components, to maintain a relatively low cost. As such, flow path element 28 may be replaced without impacting operation of the active components of detector device 30 (e.g., a composition sensor and a pump motor, as described herein). This may enhance the usability of detector device 30 in a setting in which detector device 30 is implemented in respiratory circuits for a plurality of subjects.

As can be seen in FIG. 2, detector device 30 is configured to releasably couple with flow path element 28, to cause the measurement flow of breathable gas to be drawn through flow path element 28, monitor the composition of the gas within sampling chamber 36, and/or to perform other functions. Detector device 30 may include one or more of a housing 48, element dock 50, a detector assembly 52, a pump actuator 54, pump motor 56, a controller 58, and/or other components.

Housing 48 is configured to house some or all of the components of detector device 30. Housing 48 is formed of a rigid material, such as a metallic, plastic or polymer. Housing 48 may provide mechanical protection, fluid protection, and/or other types of protection for the components of detector device 30.

Element dock 50 is configured to removably engage flow path element 28. Element dock 50 may be formed by housing 48. For example, housing 48 may have a shape at element dock 50 that accommodates the external shape of flow path element 28. Element dock 50 secures flow path element 28 to detector device 30, and places the various components of flow path element 28 and detector device 30 in the proper relative positions for use. In securing flow path element 28 to detector device 30, element dock 50 may engage flow path element 28 with one or more of a threaded engagement, an interlocking engagement, a friction fit, a snap fit, a latch, and/or other mechanisms for releasable engagement.

Detector assembly 52 is configured to monitor the composition of gas in sampling chamber 36. For example, detector assembly 52 may be configured to detect a relative level of carbon dioxide, a relative level of oxygen, anesthetic agents (e.g., nitrous oxide, halothane, desflurane, etc.), trace gases (e.g., PPM or PPB concentrations), and/or relative levels of other gas constituents within sampling chamber 36. Detector assembly may include one or more of a radiation source 60, a sensor assembly 62, windows 64, and/or other components.

Radiation source 60 is configured to emit electromagnetic radiation through sampling chamber 36 (e.g., through windows 64). The electromagnetic radiation emitted travels through the gas within sampling chamber 36, and out of sampling chamber 36 on the other side of sampling chamber 36. The electromagnetic radiation generated by radiation source 60 may have a specified set of one or more wavelengths used to detect one or more gases. By way of non-limiting example, infrared electromagnetic radiation from radiation source 60 may be implemented to monitor the relative level of carbon dioxide within sampling chamber 36. Although not shown in FIG. 2, radiation source 60 may include one or more optical elements configured to guide the emitted electromagnetic radiation into sampling chamber 36. Such elements may include one or more of a mirror, a lens, and/or other optical elements.

Sensor assembly 62 is configured to receive electromagnetic radiation emitted by radiation source 60 that has passed through sampling chamber 36, and the gas contained therein, and to generate output signals conveying information related to one or more parameters of the received electromagnetic radiation. The one or more parameters may include one or more of intensity, flux, luminescence, phase, and/or other parameters. Sensor assembly 62 includes one or more photosensitive sensors configured to generate output signals related to the intensity of received electromagnetic radiation. Sensor assembly 62 may include one or more optical elements to filter, shape, and/or guide the electromagnetic radiation to the one or more photosensitive sensors. Such optical elements may include one or more of a mirror, a half-mirror, a wavelength filter, a polarizer, a lens, and/or other optical elements. For example, the output signals may convey information related to intensity of the electromagnetic radiation in a wavelength range that is absorbed by a gaseous constituent of interest (e.g., carbon dioxide), and the intensity of electromagnetic radiation in a reference wavelength range expected to be substantially unabsorbed. As another example, the output signals may convey information related to a difference between intensity in the absorbed wavelength range and the references wavelength range.

In some embodiments, radiation source 60 and sensor assembly 62 may operate to monitor the composition of the measurement flow of the gas drawn through flow path element 28 in the manner described in U.S. Pat. No. 7,748,280, which is hereby incorporated by reference in its entirety.

This description of detector assembly 52 is not intended to be limiting. It will be appreciated that the assembly described and shown may be replaced and/or augmented with other assemblies for detecting relative levels of gaseous constituents. For example, a relative level of oxygen may be monitored with a luminescence quenching assembly that provides electromagnetic radiation into sampling chamber 36, receives electromagnetic radiation emitted by a luminescent material within sampling chamber, and generates output signals providing information related to the received electromagnetic radiation and/or the electromagnetic radiation emitted by detector assembly 52. This type of monitoring is described, for example, in U.S. Pat. Nos. 6,325,978 and 6,632,402, both of which are hereby incorporated by reference into the present application in their entirety.

Pump actuator 54 is configured to releasably engage actuator interface 46 of flow path element 28, and to actuate membrane 44 to create flow through flow path element 28. In some embodiments, actuator interface pump actuator 54 is configured to magnetically couple with actuator interface 46 to secure the engagement therebetween. This is not intended to be limiting.

Pump motor 56 is configured to drive pump actuator 54 such that pump actuator 54 actuates membrane 44 to create flow through flow path element 28. The operation of pump motor 56 can be controlled to adjust one or both of pressure and/or flow rate through flow path element 28.

Controller 58 is configured to provide processing and/or control functionality within detector device 30. As such, controller 58 may include one or more of a digital processor, an analog processor, a digital circuit designed to process information, an analog circuit designed to process information, a state machine, and/or other mechanisms for electronically processing information. Controller 58 is configured to control pump motor 56. This may include controlling pump motor 56 to adjust the pressure and/or flow rate of the measurement flow of breathable gas through flow path element 28 (e.g., in accordance with instructions received from an external device). Controller 58 is configured to control radiation source 60. This may include controlling power provided to radiation source 60, controlling one or more parameters of the electromagnetic radiation emitted by radiation source 60 (e.g., intensity), and/or other control. Controller 58 may be configured to provide some processing on the output signals generated by sensor assembly 62. This may include smoothing one or more output signals, differencing output signals, and/or other processing.

Figure 3:
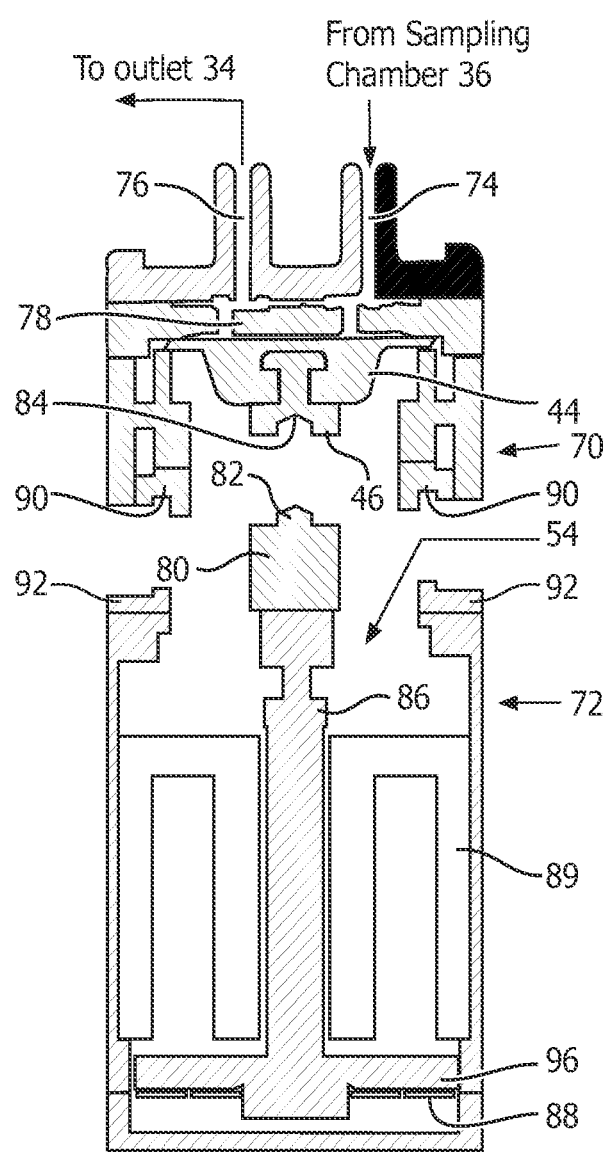
FIG. 3 is a diagram of a detector device and flow path assembly.
Figure 4:
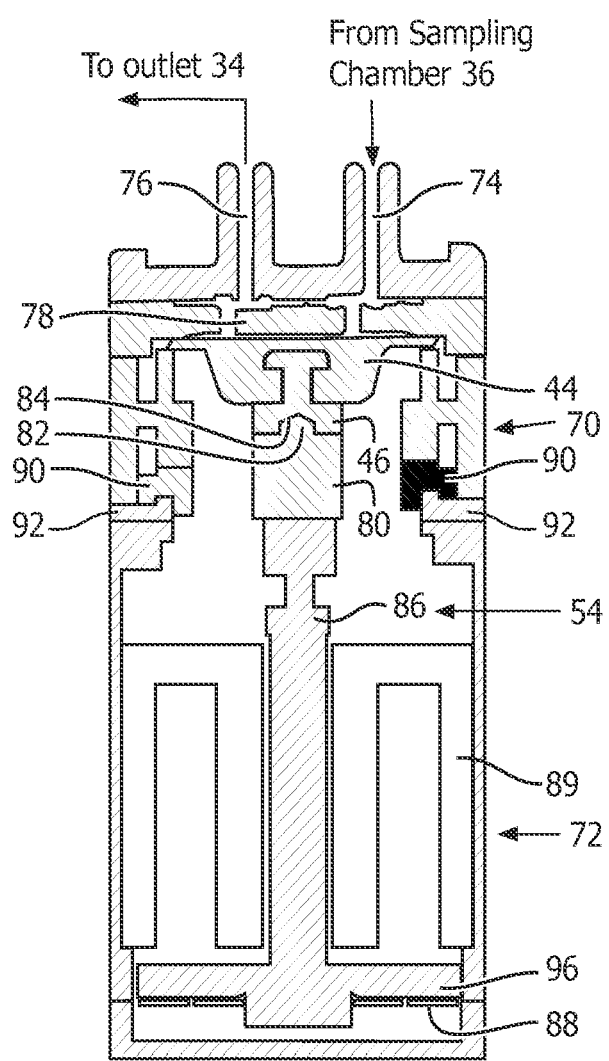
FIG. 4 is a diagram of a detector device and flow path assembly.

FIGS. 3 and 4 illustrate the operation of the pump formed by flow path element 28 and detector device 30, in some embodiments. The pump comprises a pump housing which comprises two parts 70, 72, a first part 70 (formed as a part of pump section 38 in flow path element 28 in FIGS. 1 and 2) in which membrane 44, an inlet 74 and an outlet 76 are arranged, and a second part 72 (formed as a part of detector device 30 in FIGS. 1 and 2) in which pump actuator 54 is arranged. Membrane 44 is mounted to the first part 70 of the pump housing and delimits a pump chamber 78 inside said first part 70. The inlet 74, which has a first non-return valve (not shown) connected thereto, is arranged for feeding the measurement flow of breathable gas into the pump chamber 78, and the outlet 76, which has a second non-return valve (not shown) connected thereto, is arranged for discharging the measurement flow of breathable gas from the pump chamber 78. The pump actuator 54 is configured for moving the membrane 44 back and forth between a first and a second position when the pump is in its assembled form and in use. The membrane 44 is configured to be detachably connected to the pump actuator 54 by means of a magnetic coupling, which comprises actuator interface 46 fixed to the membrane 44 and a corresponding magnetic coupling part 80 fixed to the pump actuator 54. The magnetic coupling can be achieved by having one of the actuator interface 46 and the magnetic coupling part 80 comprising a permanent magnet and the other comprising a ferromagnetic material. The magnetic coupling can of course instead comprise two permanent magnets, one permanent magnet comprised in the actuator interface and one in the magnetic coupling part 80. An electromagnetic coupling is of course also possible. Preferably, the actuator interface 46 comprises a ferromagnetic material and the magnetic coupling part 80 comprises a permanent magnet. The magnetic coupling part 80 also comprises a protrusion 82 configured for insertion into a corresponding recess 84 comprised in the actuator interface 46. Of course a protrusion instead can be comprised in the actuator interface 46 for insertion into a corresponding recess comprised in the magnetic coupling part 80. The pump actuator 54 comprises a shaft 86, which at one end is provided with said magnetic coupling part 80. To move the membrane 44 back and forth the shaft 86 of the pump actuator 54 is driven by a spring, preferably a flat spring 88, longitudinally in one direction and an electromagnet 89 longitudinally in the opposite direction. The spring 88 can of course be replaced by a second electromagnet.

The first part 70 of the pump housing is detachably connected to the second part 72 of the pump housing by means of a coupling, which coupling comprises a first coupling part 90 fixed to the first part 70 of the pump housing and a second coupling part 92 fixed to the second part 72 of the pump housing. The coupling of the pump housing shown in FIGS. 3 and 4 is a magnetic coupling, wherein one of the first 90 and second 92 coupling parts comprises a permanent magnet and the other coupling part comprises a ferromagnetic material. The magnetic coupling can of course instead comprise two permanent magnets, one permanent magnet comprised in the first coupling part 90 and one in the second coupling part 92. Preferably the first coupling part 90 comprises a ferromagnetic material and the second coupling part 92 comprises a permanent magnet. The coupling of the pump housing can also be a snap coupling or any other mechanical or electromechanical coupling suitable for the purpose of connecting the first 70 and the second 72 parts of the pump housing to each other.

The first part 70 of the pump housing is exchangeable (e.g., along with the rest of flow path element 28) and in order to detach it from the second part 72 of the pump housing (and/or detector device 30) said first part 70 is moved in the longitudinal direction of said shaft 86 away from the second part 72 of the pump housing, whereby the actuator interface 46 is detached from the magnetic coupling part 80 and the first coupling part 90 of the pump housing is detached from the second coupling part 92 of the pump housing. If the coupling of the pump housing is a snap coupling or any other coupling, other operations may be needed for detaching the first part 70 of the pump housing from the second part 72 of the pump housing. To attach the first part 70 of the pump housing to the second part 72 of the pump housing the two parts 70, 72 of the pump housing are moved towards each other so as to allow the corresponding coupling parts to come into engagement with each other.

Figure 5:
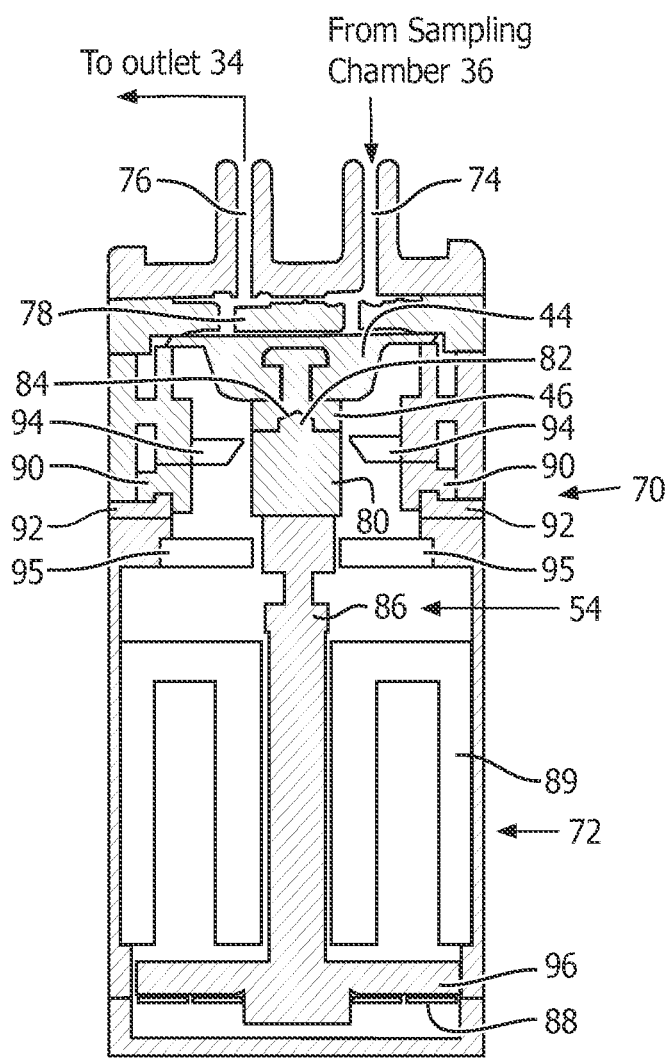
FIG. 5 is a diagram of a detector device and flow path assembly.

In the embodiments illustrated in FIG. 5, the pump comprises guiding means 94 configured for radially guiding the shaft 86 of the pump actuator 54 so as to guide the protrusion 82 of the magnetic coupling part 80 into the recess 84 of the pump actuator 54 when the first part 70 of the pump housing is connected to the second part 72 of the pump housing. The guiding means 94 of the first part 70 of the pump housing has a central opening configured for receiving said shaft 86 and/or the magnetic coupling part 80. The second part 72 of the pump housing comprises guiding means 95 configured for restricting radial movement of the shaft 86 in said second part 72 of the pump housing. The guiding means 95 of the second part 72 of the pump housing is especially important when the first part 70 of the pump housing is detached, due to the risk for damaging the shaft 86 by having it hit the electromagnet 89 if said guiding means 95 is absent. The guiding means 95 of the second part 72 of the pump housing has a central opening configured for receiving said shaft 86.

During pumping using the pumps shown in FIGS. 3-5, in a first phase the flat spring 88 affects the shaft 86, and thereby the membrane 44, with a force pulling the membrane 44 in a direction away from the pump chamber 78, whereby the volume of the pump chamber 78 expands and the first non-return valve is opened so as to allow the measurement flow of breathable gas to flow into the pump chamber 78 through the inlet 74. During this first phase, the membrane 44 is moved under the action of the spring 88 from a first end position to a second end position. In a second phase the electromagnet 89 is activated, whereby the electromagnet 89 attracts a protruding magnetic part 96 of the shaft 86 and the shaft 86 is pulled in a direction towards the pump chamber 78, and the membrane 44 consequently also moves towards the pump chamber 78. The pump chamber 78 is thereby contracted and the measurement flow of breathable gas flows out from the pump chamber 78 through the second non-return valve and the outlet 76. During this second phase, the membrane 44 is moved under the action of the electromagnet 89 and against the action of the spring 88 from the second end position to the first end position. Of course another electromagnet can replace the spring 88 and provide the force for pulling the membrane 44 away from the pump chamber 78. If the spring 88 is replaced by an electromagnet, the other electromagnet 89 can be replaced by another spring, which provides the force for pushing the membrane 44 towards the pump chamber 78. By way of non-limiting example, the pump may operate as described in WIPO publication no. WO2010/128914, which is hereby incorporated by reference in its entirety.

In some embodiments, operation of the pumps shown in FIGS. 3-5 may be precise enough that one or more parameters of the measurement flow of breathable gas can be determined, inferred, and/or adequately estimated without further monitoring. Such parameters may include, for example, pressure, flow rate, and/or other parameters. In some embodiments, one or more detectors may be included with the pumps to directly measurement one or more parameters of the measurement flow of breathable gas. For example, a sensor may be held in second part 72 that contacts membrane 44. The output signals generated by the sensor may indicate one or more of a pressure applied by membrane 44, movement of membrane 44, and/or other parameters. This output signal may facilitate determination of the pressure and/or flow rate of the measurement flow of breathable gas through pump chamber 78. As another non-limiting example, a pressure and/or flow rate detector may be included within first part 70 to directly measure the pressure and/or flow rate of measurement flow of breathable gas. In such embodiments, electrical contacts may be included on first part 70 and/or second part 72 to facilitate communications of the output signals of such detectors to a controller (e.g., controller 58 in FIG. 2).

Figure 6:
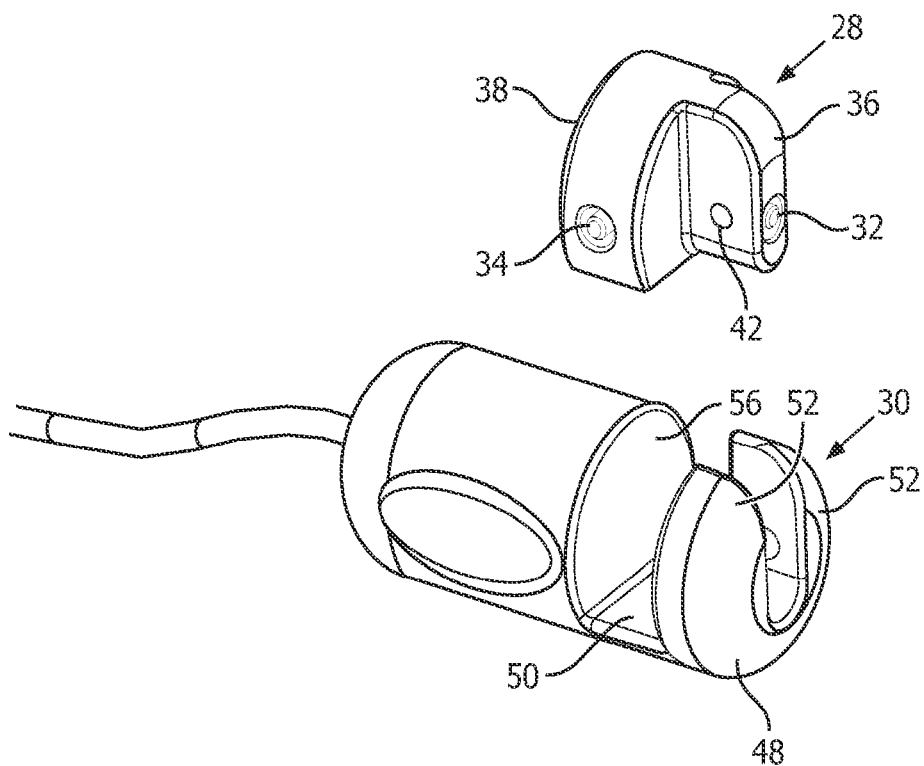
FIG. 6 is a diagram of a detector device and flow path assembly.
Figure 7:
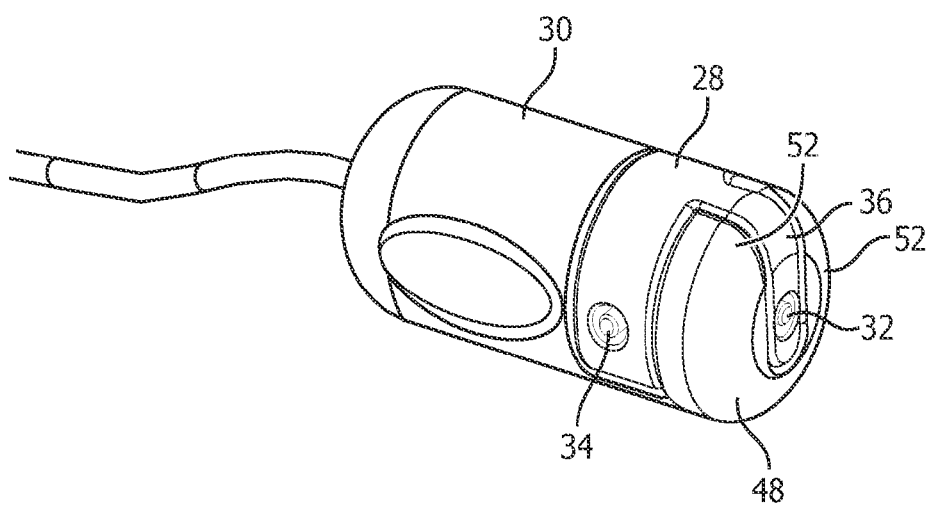
FIG. 7 is a diagram of a detector device and flow path assembly.

FIGS. 6 and 7 illustrate flow path element 28 and detector device 30 having different form factors than illustrated in FIGS. 1 and 2. In particular, in the embodiments illustrated in FIGS. 6 and 7, flow path element 28 and detector device 30 have a generally cylindrical shape.

Figure 8:
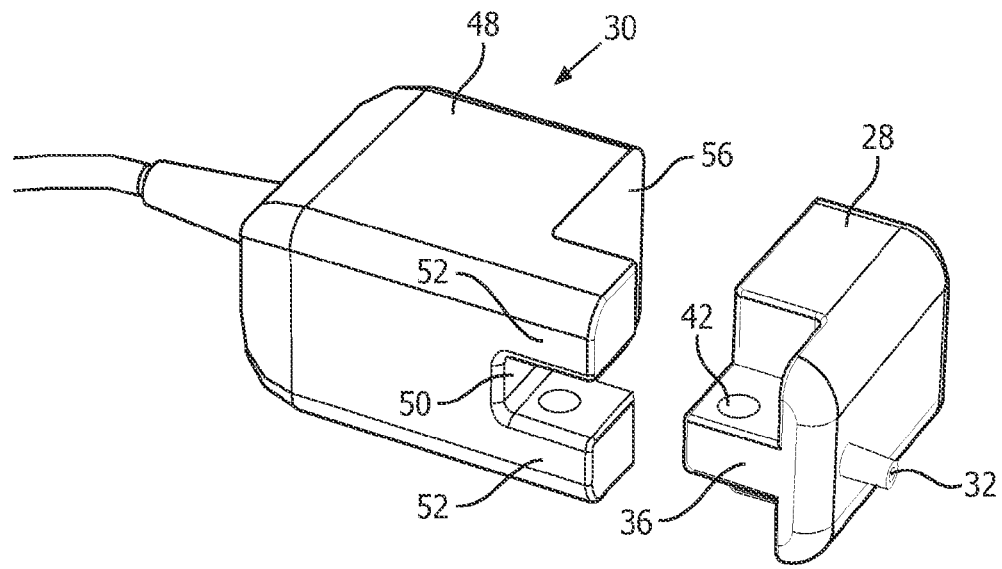
FIG. 8 is a diagram of a detector device and flow path assembly.
Figure 9:
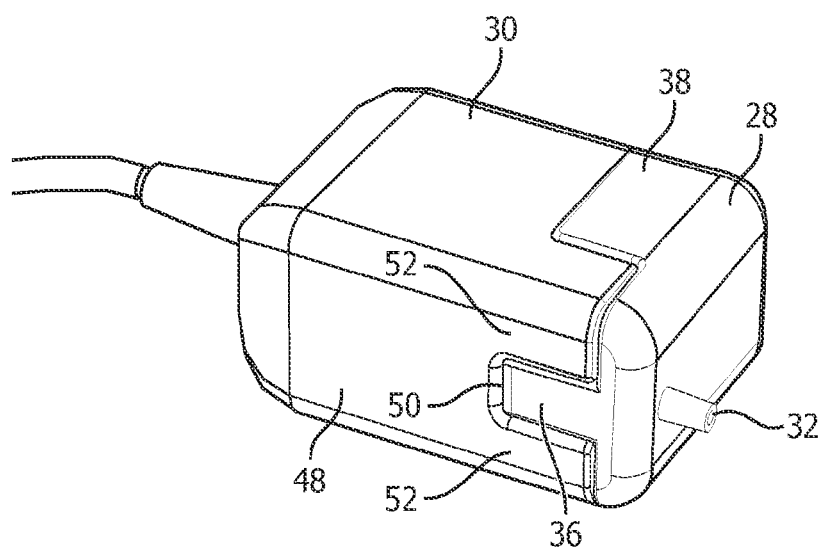
FIG. 9 is a diagram of a detector device and flow path assembly.

FIGS. 8 and 9 illustrate one or more embodiments in which flow path element 28 and detector device 30, when assembled for operation, have a generally rectangular shape.

Figure 10:
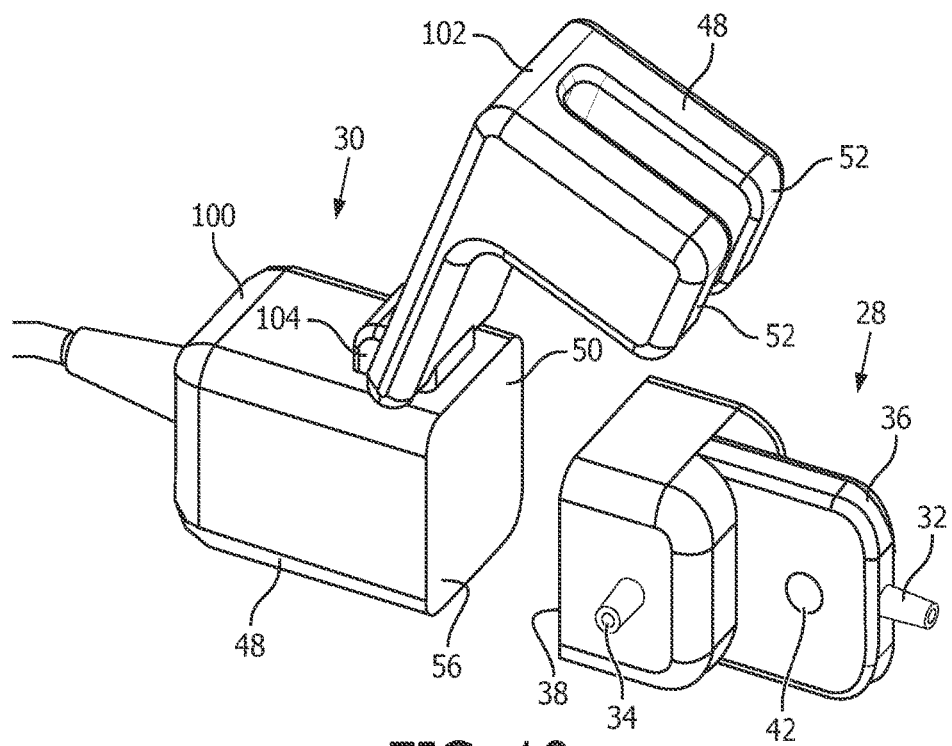
FIG. 10 is a diagram of a detector device and flow path assembly.
Figure 11:
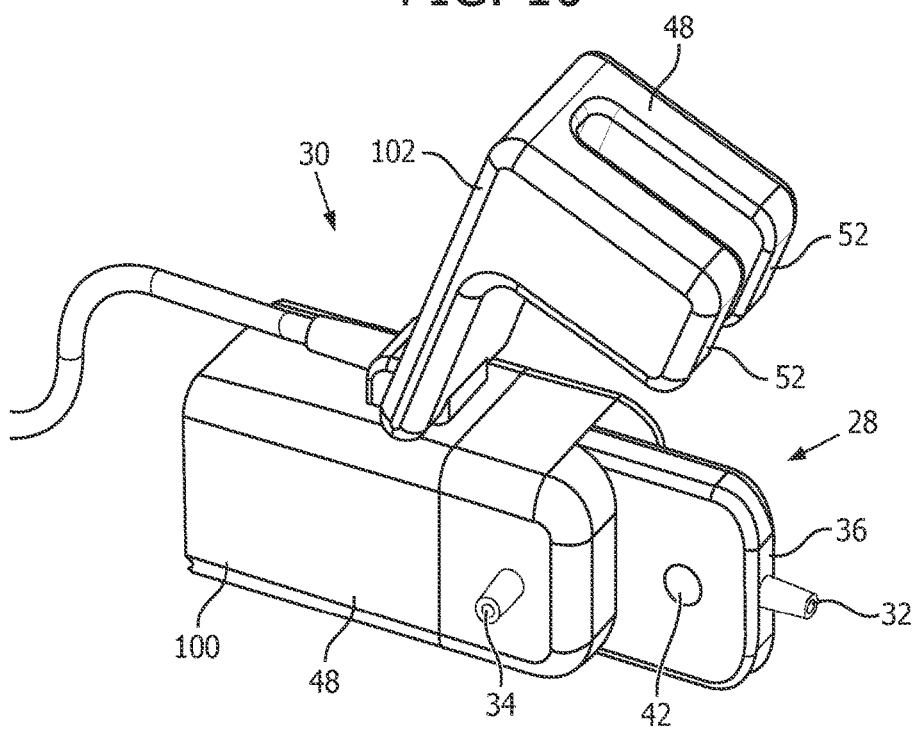
FIG. 11 is a diagram of a detector device and flow path assembly.
Figure 12:
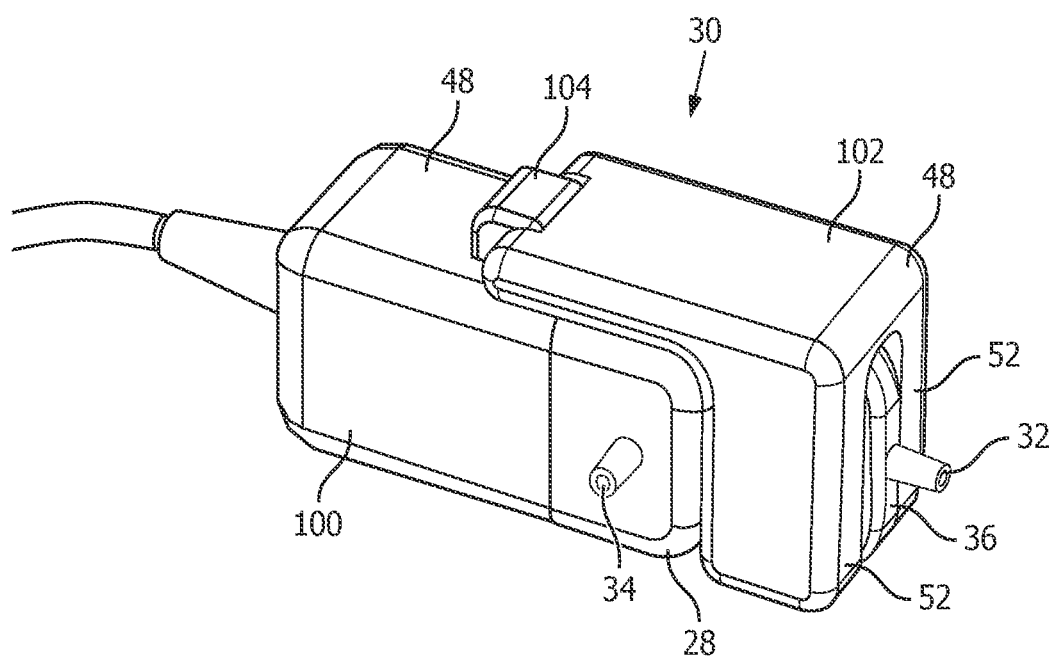
FIG. 12 is a diagram of a detector device and flow path assembly.

FIGS. 10-12 illustrate one or more embodiments in which housing 48 includes a first section 100 and a second section 102. First section 100 and second section 102 are joined by a pivotal connection 104. First section 100 carries pump actuator 54 and pump motor 56. Second section 102 carries detector assembly 52. To assemble flow path element 28 and detector device 30, flow path element 28 is positioned on first section 100 (e.g., as shown in FIG. 11), and then second section 102 is pivoted into place (e.g., ad shown in FIG. 12). The pivoting of second section 102 with respect to first section 100 and flow path element 28, positions detector assembly 52 properly with respect to sampling chamber 36 of flow path element 28 so that detector assembly 52 can access windows 42. The pivoting of second section 102 further may enhance the security of the physical engagement between flow path element 28 and detector device 30.

Figure 13:
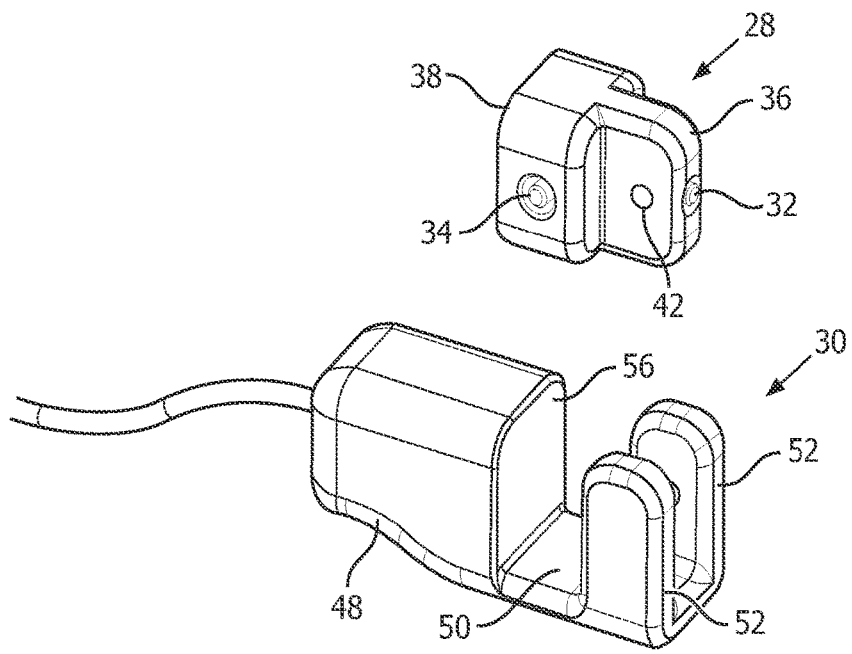
FIG. 13 is a diagram of a detector device and flow path assembly.
Figure 14:
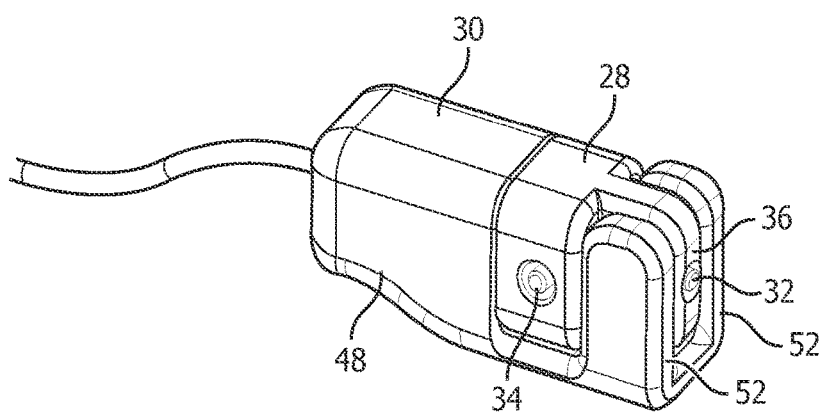
FIG. 14 is a diagram of a detector device and flow path assembly.

FIGS. 13 and 14 illustrate one or more embodiments in which flow path element 28 and detector device 30, when assembled for operation, have a generally rectangular shape.

Figure 15:
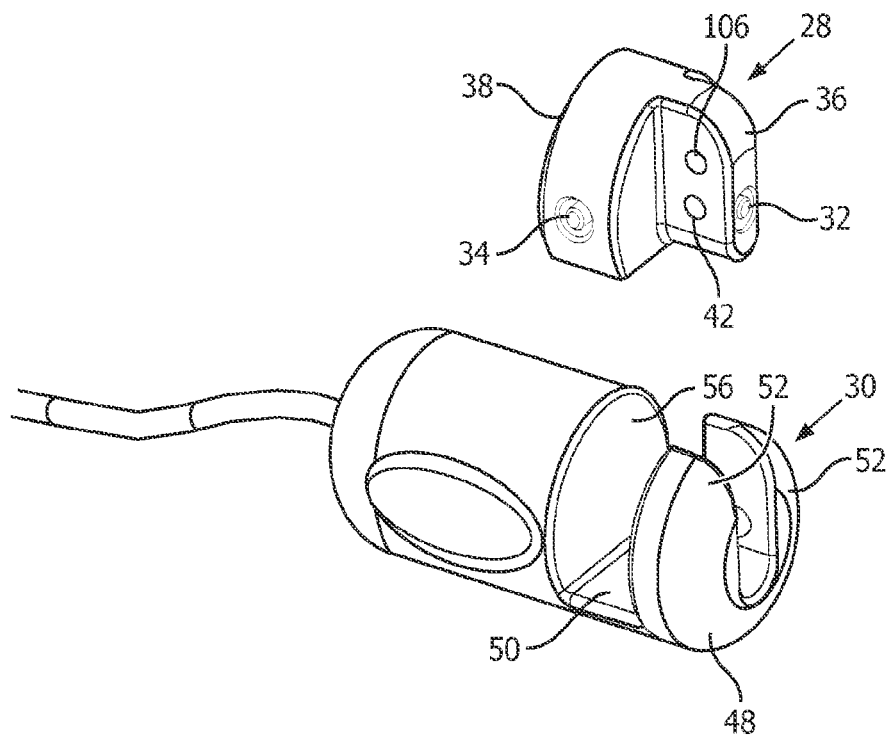
FIG. 15 is a diagram of a detector device and flow path assembly.
Figure 16:
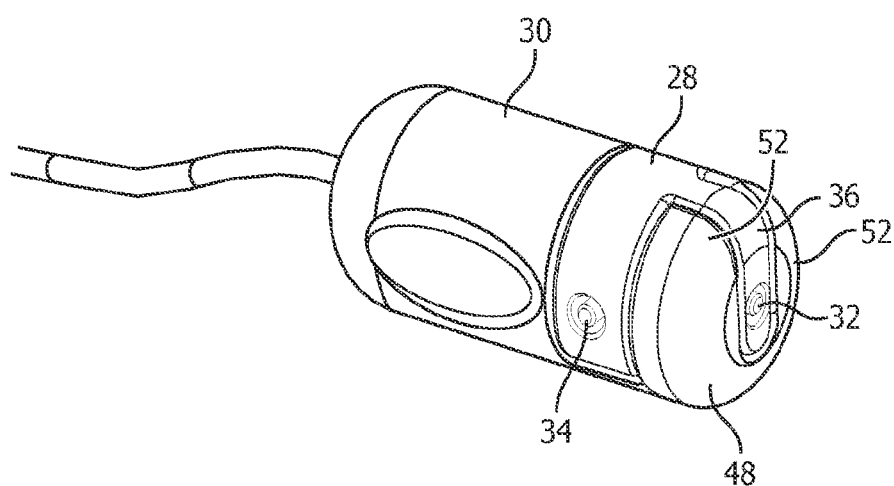
FIG. 16 is a diagram of a detector device and flow path assembly.

FIGS. 15 and 16 illustrate one or more embodiments in which detector assembly 52 create a plurality of optical paths through sampling chamber 36. For example, a first optical path may be associated with a sensor assembly designed to determine a relative level of carbon dioxide within sampling chamber 36, and a second optical path may be associated with a sensor assembly designed to determine a relative level of one or more other gaseous constituents using, without limitation, luminescence quenching. To facilitate the second optical path, flow path element 28 includes a window 106 in addition to window 42, to enable electromagnetic radiation to be guided into sampling chamber 36 from two separate radiation sources within detector assembly 52.

Figure 17:
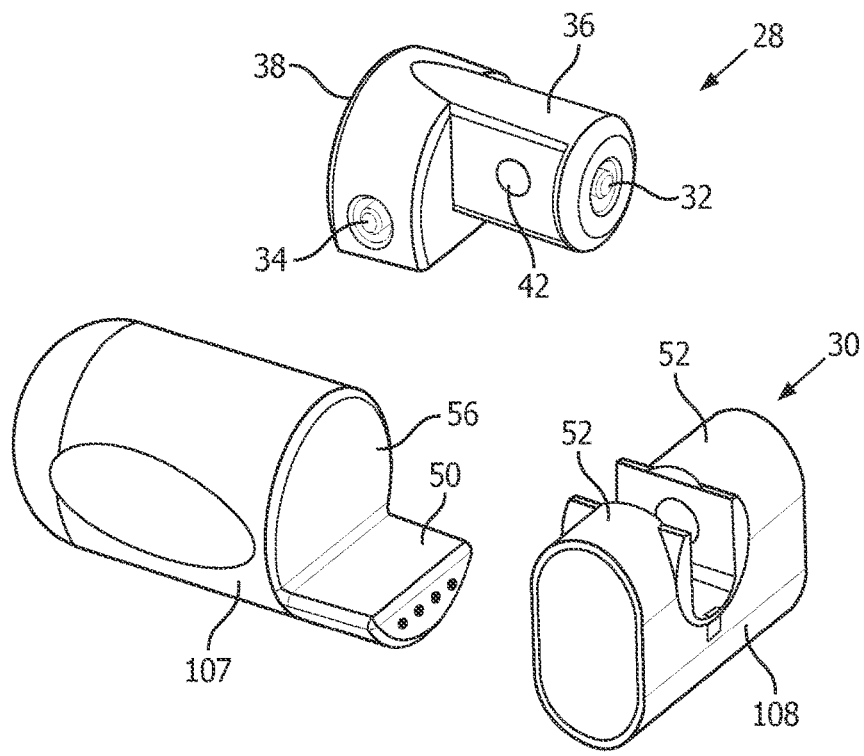
FIG. 17 is a diagram of a detector device and flow path assembly.
Figure 18:
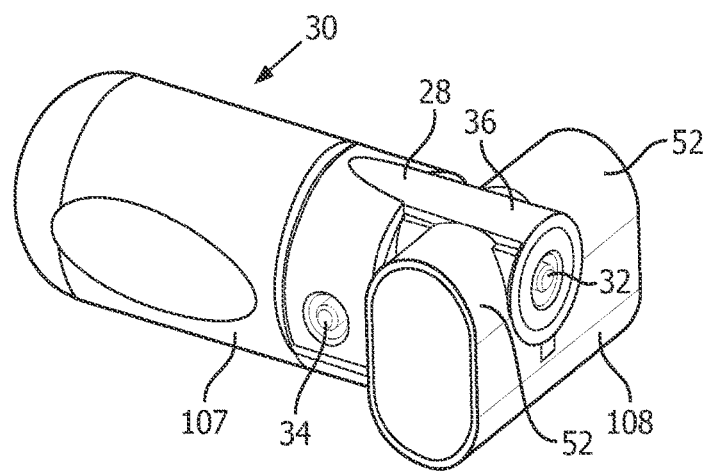
FIG. 18 is a diagram of a detector device and flow path assembly.

FIGS. 17 and 18 illustrate one or more embodiments in which detector device 30 comprises two separate components. Specifically, detector device 30 includes a pump subsystem 107 and a sampling subsystem 108. Pump subsystem 107 and sampling subsystem 108 may be removably docked with each other during use. Pump subsystem 107 and/or sampling subsystem 108 removably engage with flow path element 28 during use to monitor one or more parameters of the measurement flow of breathable gas through flow path element 28 (e.g., as described above). Pump subsystem 107 carries the components disposed within detector device 30 associated with the pump. Sampling subsystem 108 carries the components of detector assembly 52. In some embodiments, sampling subsystem 108 and detector assembly 52 are configured to also operate with a mainstream airway adapter (not shown), and mating sampling subsystem 108 with pump subsystem 107 to sample gas within flow path element 28 may extend the functionality of sampling subsystem 108 beyond use in a mainstream system. During such operation, a mainstream airway adapter may be removably engaged with sampling subsystem 108 between the portions of detector assembly 52 in much the same was a flow path element 28 is in FIG. 18. By way of further explanation, U.S. patent application Ser. No. 14/113,543 entitled "Mainstream Gas Analyzer Configurable To Removably Couple With A Sidestream Gas Sampling Component" provides a description of a mainstream sampling assembly that is usable with a pump to extend the functionality and usability of the sampling assembly. U.S. patent application Ser. No. 14/113,543 is hereby incorporated by reference in its entirety. Pump subsystem 107 may be powered by a battery carried within pump subsystem. In these embodiments, wired links between pump subsystem 107 and sampling subsystem 108 may not be need/provided. In some embodiments, pump subsystem 107 and sampling subsystem 108 may be coupled through electrical contacts (and/or other electronic couplings) to facilitate communication of control, output, and/or power between pump subsystem 107 and sampling subsystem 108.

Figure 19:
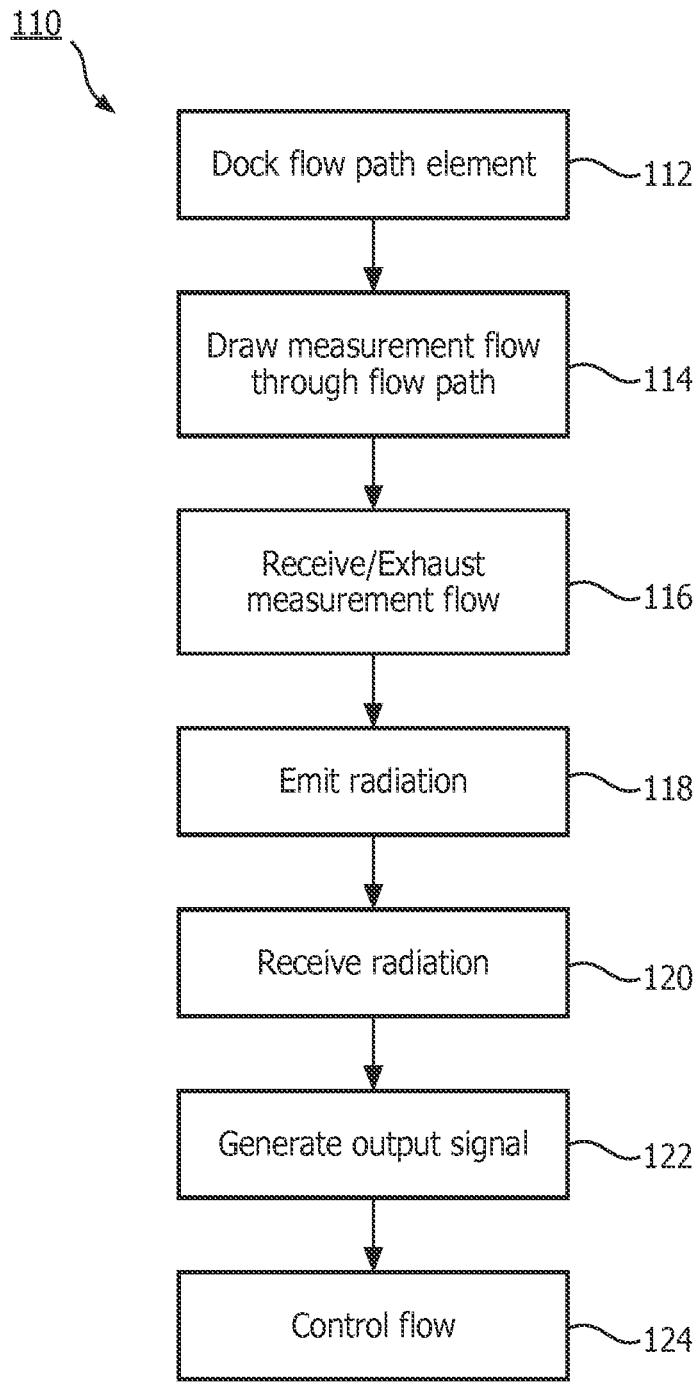
FIG. 19 is a method of monitoring composition of a flow of breathable gas being delivered to a subject.

FIG. 19 illustrates a method 110 of measuring the composition of a flow of breathable gas received from a respiratory circuit. The operations of method 110 presented below are intended to be illustrative. In some embodiments, method 110 may be accomplished with one or more additional operations not described, and/or without one or more of the operations discussed. Additionally, the order in which the operations of method 110 are illustrated in FIG. 19 and described below is not intended to be limiting.

At an operation 112, a flow path element is docked with a housing of a detector device. The flow path element has an inlet and an outlet, and forms an enclosed flow path therebetween. In some embodiments, operation 112 may be performed by a detector device docking a flow path element the same as or similar to the docking of detector device 30 and flow path element 28 (shown in FIGS. 1-18 and described herein).

At an operation 114, a measurement flow of breathable gas is drawn through the flow path element. This may include actuating one or more components of the flow path element to draw gas through the enclosed flow path. In some embodiments, operation 114 is performed by a pump motor and pump actuator the same as or similar to pump motor 56 and pump actuator 54, respectively (shown in FIGS. 2-5 and described herein).

At an operation 116, the measurement flow of breathable gas is received into the, and/or exhausted from the flow path element. The measurement flow of breathable gas may be obtained in a sidestream fashion from a flow of breathable gas being delivered to a subject through a respiratory circuit. In some embodiments, operation 114 is performed by a flow path element the same as or similar to flow path element 28 (shown in FIGS. 1-18 and described herein).

At an operation 118, electromagnetic radiation is emitted into the flow path element. The electromagnetic radiation may be emitted into a sampling chamber formed within the flow path element. In some embodiments, operation 118 is performed by a radiation source the same as or similar to radiation source 60 (shown in FIGS. 1 and 2, and described herein).

At an operation 120, electromagnetic radiation that has been emitted by the radiation source, and has passed through the flow path element, is received onto a sensor assembly. In some embodiments, operation 120 is performed by a sensor assembly the same as or similar to sensor assembly 62 (shown in FIGS. 1-2 and described herein).

At an operation 122, output signals conveying information related to the intensity of the electromagnetic radiation received at operation 120 are generated. These output signals may facilitate determinations of composition of the gas within the flow path element (e.g., carbon dioxide level, oxygen level, and/or other compositional measurements. In some embodiments, operation 122 is performed by a sensor assembly the same as or similar to sensor assembly 62 (shown in FIGS. 1-2 and described herein).

At an operation 124, actuation of the one or more components of the flow element is controlled to control the flow rate and/or the pressure of the measurement flow of breathable gas through the enclosed flow path. In some embodiments, operation 124 is performed by a controller the same as or similar to controller 58 (shown in FIG. 2 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A detector device configured to measure composition of a flow of breathable gas received from a respiratory circuit, the detector device comprising:
   a housing;
   a removable flow path element forming an enclosed flow path for the flow of breathable gas, the removable flow path element comprising an inlet, a sampling chamber, a pump section including a membrane and an actuator interface coupled to the membrane, and an outlet, wherein the inlet and the outlet of the removable flow path element are positioned on adjacent sides of the housing;
   a flow path element dock formed by the housing, the flow path element dock being configured to removably engage the removable flow path element;
   a radiation source housed within the housing configured to emit electromagnetic radiation into the sampling chamber of the removable flow path element while the removable flow path element is docked in the flow path element dock;
   a sensor assembly housed within the housing configured such that, while the removable flow path element is docked in the flow path element dock and the radiation source emits electromagnetic radiation into the sampling chamber of the removable flow path element, the sensor assembly receives electromagnetic radiation that has been emitted by the radiation source and has passed through the flow path formed in the removable flow path element, the sensor assembly being further configured to generate an output signal conveying information related to one or more parameters of the received electromagnetic radiation for determining the composition of the breathable gas in the enclosed flow path;
   a pump actuator carried by the housing in a separate portion from the removable flow path element and driven by a pump, the pump actuator being configured to move the membrane in the pump section of the removable flow path element by moving the actuator interface to draw the flow of breathable gas through the enclosed flow path;
   a pressure sensor that contacts the membrane and is configured to measure a flow rate of the flow of breathable gas; and
   a controller housed within the housing configured to control both:
      (i) the pump actuator to maintain the flow rate of the flow of breathable gas through the enclosed flow path; and
      (ii) power provided to the radiation source;
   wherein the housing comprises:
      a first section carrying the pump actuator and a pump motor, the removable flow path element being positioned on the first section; and
      a second section carrying the radiation source, the sensor assembly and the controller, and the second section being configured to pivot with respect to the first section and the removable flow path element.

2. The detector device of claim 1, wherein the pump actuator is further configured to detachably connect to the actuator interface of the removable flow path element.

3. The detector device of claim 1, wherein the pump actuator carries a magnet configured to magnetically couple the removable flow path element to the pump actuator.

4. The detector device of claim 3, wherein the magnet is a first magnet, the actuator interface includes a second magnet configured to magnetically couple to the first magnet, the first magnet and the second magnet comprising at least one of a permanent magnet, a ferromagnet and an electromagnetic magnet, and the first magnet comprises a protrusion configured for insertion into a corresponding recess of the actuator interface.

5. The detector device of claim 3, wherein the pump actuator comprises a shaft with the magnet positioned at one end, the detector device comprising a spring, wherein the pump actuator is configured to be driven by the spring longitudinally in a first direction and the magnet longitudinally in an second direction opposite the first direction to move the membrane in corresponding first and second directions.

6. The detector device of claim 1, wherein the outlet of the removable flow path element is connected with the respiratory circuit to exhaust the flow of breathable gas from the removable flow path element to the respiratory circuit.

7. The detector device of claim 1, wherein the sampling chamber of the removable flow path element is orthogonal to the pump section of the removable flow path element.

8. The detector device of claim 1, wherein the housing has a shape at the flow path element dock that is configured to accommodate a corresponding external shape of the removable flow path element, and wherein the flow path element dock is configured to removably engage the removable flow path element via at least one of a threaded engagement, an interlocking engagement, a friction fit and a snap fit.

9. The detector device of claim 1, wherein the removable flow path element is configured to be removably coupled to the housing via a magnetic coupling.

10. The detector device of claim 1, wherein the removable flow path element comprises a first guide configured to radially guide a shaft of the pump actuator to couple with the actuator interface, and wherein the housing comprises a second guide configured to restrict radial movement of the shaft, the first and second guides having a central opening to receive the shaft.

11. The detector device of claim 1, wherein the membrane is a movable membrane and the removable flow path element comprises a rigid wall with an opening covered by the movable membrane.

12. The detector device of claim 1, wherein the radiation source is a first radiation source configured to emit a first electromagnetic radiation, the detector device comprising a second radiation source separate from the first radiation source, the second radiation source configured to emit a second electromagnetic radiation in an optical path separate from an optical path of the first radiation source through the sampling chamber, wherein each of the separate optical paths is configured to be associated with a respective sensor of the sensor assembly, and wherein each respective sensor is configured to determine a level of a different gaseous constituent of the flow of breathable gas.

13. The device of claim 1, wherein the second section is configured such that when the second section engages the flow path element, the detector assembly is configured to access a window of the flow path element.

14. A method of measuring composition of a flow of breathable gas received from a respiratory circuit, the method comprising acts of:
   removably docking a flow path element with a housing of a detector device, the removable flow path element having an inlet, a sampling chamber, a pump section comprising a membrane and an actuator interface coupled to the membrane, and an outlet, wherein the inlet and the outlet of the removable flow path element are positioned on adjacent sides of the housing;

emitting electromagnetic radiation from a radiation source into the sampling chamber of the removable flow path element while the removable flow path element is docked with the housing, wherein the radiation source is housed within the housing;

receiving electromagnetic radiation that has been emitted by the radiation source and has passed through an enclosed flow path of the removable flow path element onto a sensor assembly housed within the housing;

generating an output signal conveying information related to one or more parameters of the electromagnetic radiation received onto the sensor assembly;

actuating the membrane of the flow path element by moving the actuator interface of the removable flow path element through movement of a pump actuator carried by the housing in a separate portion from the removable flow path element to draw the flow of breathable gas through the enclosed flow path;

controlling, with a controller housed within the housing:
(i) the pump actuator to maintain a flow rate of the flow of breathable gas through the enclosed flow path; and
(ii) an intensity of the radiation source; and measuring the flow rate of the breathable gas with a pressure sensor directly contacting the membrane;

wherein the housing comprises:
a first section carrying the pump actuator and a pump motor, the removable flow path element being positioned on the first section; and
a second section carrying the radiation source, the sensor assembly and the controller, and the second section being configured to pivot with respect to the first section and the removable flow path element.

15. The method of claim 14, further comprising an act of: driving the pump actuator by the pump motor for actuating membrane of the flow path element to draw the flow of breathable gas through the enclosed flow path.

16. The method of claim 14, wherein the pump actuator carries a magnet configured to magnetically couple the flow path element to the pump actuator via the actuator interface.

17. The method of claim 14, further comprising acts of: receiving the flow of breathable gas into the inlet of the removable flow path element; and
exhausting the flow of breathable gas out of the outlet of the removable flow path element.

18. The method of claim 17, wherein the exhausting act comprises exhausting the flow of breathable gas from the removable flow path element back into the respiratory circuit.

19. A detector device for measuring composition of a flow of breathable gas received from a respiratory circuit, the detector device comprising:
a housing means for housing the detector device;
a docking means for removably docking a removable flow path element with the housing means the detector device, the removable flow path element having an inlet, a sampling chamber, a pump section including a movable membrane, an actuator interface coupled to the movable membrane, and an outlet, wherein the inlet and the outlet of the removable flow path element are positioned on adjacent sides of the housing means;

a radiation emitting means for emitting electromagnetic radiation into the sampling chamber of the removable flow path element while the removable flow path element is docked with the housing means, wherein the radiation emitting means for emitting electromagnetic radiation is housed within the housing means;

a radiation receiving means for receiving electromagnetic radiation that has been emitted by the radiation emitting means for emitting and has passed through the sampling chamber of the removable flow path element, wherein the radiation receiving means for receiving is housed within the housing means;

a generating means for generating an output signal conveying information related to one or more parameters of the electromagnetic radiation received onto the radiation receiving means for receiving;

an actuating means for actuating the movable membrane in the pump section of the removable flow path element through movement of the actuator interface to draw the flow of breathable gas through the sampling chamber, wherein the actuating means for actuating is carried by the housing means in a separate portion from the removable flow path element;

a pressure sensing means for pressure sensing that contact the membrane and measure a flow rate of the flow of breathable gas; and a control means for controlling that control:
(i) the actuating means for actuating to maintain the flow rate of the flow of breathable gas through the sampling chamber; and
(ii) an intensity of the radiation emitting means for emitting electromagnetic radiation;

wherein the housing means comprises:
a first section carrying the actuating means for actuating and a pump motor, the removable flow path element being positioned on the first section; and
a second section carrying the radiation emitting means for emitting electromagnetic radiation, the radiation receiving means for receiving electromagnetic radiation and the control means for controlling, and the second section being configured to pivot with respect to the first section and the removable flow path element.

20. The detector device of claim 19, wherein the actuating means for actuating carries magnetically coupling means for magnetically coupling the actuator interface in the pump section of the removable flow path element to the actuating means for actuating.

21. The detector device of claim 19, further comprising:
flow receiving means for receiving the flow of breathable gas into the inlet of the removable flow path element and flow exhausting means for exhausting the flow of breathable gas out of the outlet of the removable flow path element.

22. The detector device of claim 21, wherein the flow exhausting means for exhausting the flow of breathable gas out of the outlet of the removable flow path element is configured to exhaust the flow of breathable gas from the removable flow path element back into the respiratory circuit.

* * * * *